(12) United States Patent
Ostrov et al.

(10) Patent No.: US 6,842,909 B2
(45) Date of Patent: Jan. 18, 2005

(54) PROTECTIVE FACE SHIELD

(76) Inventors: Holly Ostrov, 200 E. 61st St., New York, NY (US) 10021; Rita D. Brettler, 25 Mott St., Oceanside, NY (US) 11572

(*) Notice: Subject to any disclaimer, the term of this patent is extended or adjusted under 35 U.S.C. 154(b) by 0 days.

(21) Appl. No.: 10/407,076

(22) Filed: Apr. 3, 2003

(65) Prior Publication Data

US 2004/0194191 A1 Oct. 7, 2004

(51) Int. Cl.[7] ............................................. A42B 1/00
(52) U.S. Cl. .................... 2/9; 2/174; 132/319
(58) Field of Search ........................... 2/9, 174, 11, 15, 2/12, 206; 132/319; D28/9; D29/108; 128/857; 16/422

(56) References Cited

U.S. PATENT DOCUMENTS

| | | | | |
|---|---|---|---|---|
| 1,890,628 A | * | 12/1932 | Sueta et al. | 132/319 |
| 2,355,283 A | * | 8/1944 | Diss | 2/174 |
| 2,425,690 A | * | 8/1947 | Strong | 2/8 |
| 3,060,445 A | * | 10/1962 | Brockman | 2/9 |
| 3,602,913 A | * | 9/1971 | Neese | 2/9 |
| 3,740,768 A | * | 6/1973 | McCosker | 2/174 |
| 3,772,707 A | * | 11/1973 | Alosi et al. | 2/174 |
| 3,918,448 A | * | 11/1975 | McCosker | 2/9 |
| D245,545 S | | 8/1977 | Chou | |
| 4,993,617 A | * | 2/1991 | Yang | 2/11 |
| 5,538,014 A | * | 7/1996 | Wilson et al. | 132/319 |
| 5,561,855 A | * | 10/1996 | McFall | 2/8 |
| 5,797,141 A | | 8/1998 | Morlett | |
| 5,822,801 A | | 10/1998 | Varney | |
| 5,865,196 A | * | 2/1999 | Foote | 132/319 |
| D428,200 S | * | 7/2000 | Webster | D28/9 |
| 6,199,560 B1 | * | 3/2001 | North et al. | 132/319 |

* cited by examiner

Primary Examiner—Rodney M. Lindsey
(74) Attorney, Agent, or Firm—Jeffrey Sonnabend

(57) ABSTRACT

A protective face shield comprising a mask portion and a handle portion, the mask portion having an exterior surface and an interior surface. The mask portion is readily operatively attachable to and removable from the handle portion, and the interior surface definines a cavity adapted to accept a substantial portion of a users face.

10 Claims, 5 Drawing Sheets

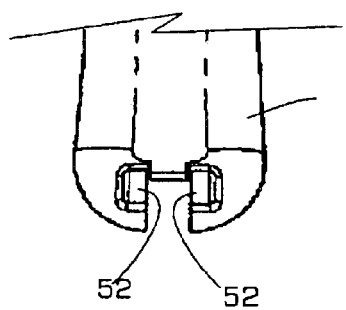
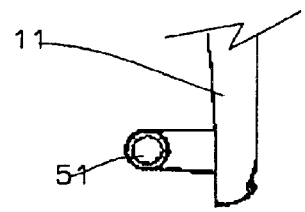
Fig. 8a
Fig. 8b
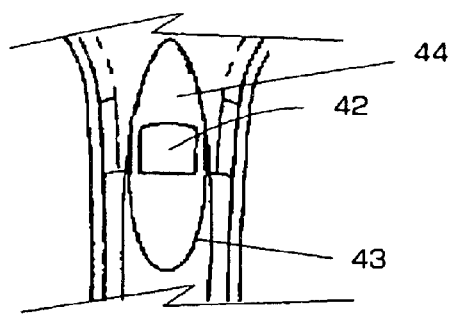
Fig. 9a
Fig. 9b

PROTECTIVE FACE SHIELD

BACKGROUND OF THE INVENTION

1. Field of the Invention

The present invention relates generally to the field of protective coverings for the face, and more specifically to protective coverings for the face for use in connection with the application of hair treatments.

2. Background of the Related Art

Modem hair treatments often require the application of various liquid, aerosol, non-aerosol pumped, non-aerosol sprayed and/or powdered products to the hair. As these treatments are applied, recipients of the treatment often experience the undesirable side effect of incidental application of the liquid, aerosol and/or powder to areas other than the hair, including incidental application to the recipient's face. Such incidental application to the face may have the undesirable effects of: disturbing previously applied cosmetics; irritating skin and eyes; entering the recipient's mouth, where they may be ingested accidentally; and/or dirtying the user's face.

Various attempts have been made to alleviate this problem; however, none has provided a satisfactory solution. For example, U.S. Pat. No. D245,545 discloses the design for a one piece face mask with mask portion and integrated handle portion. The disclosed design includes no means for allowing fresh air to reach easily the user's mouth and nose, and does not permit any exchange of the mask portion with the handle portion. As a result, the mask portion may become dirty, damaged and/or otherwise caked with hair care treatments. If the hair care treatment is a hair dying product, the mask portion may become permanently discolored. In either event, the entire face mask would need either to be cleaned or discarded if cleaning were impossible or impracticable.

U.S. Pat. No. 5,797,141 discloses a face shield with a mask portion and handle portion. The mask includes no means for providing fresh air to reach easily the user's mouth and nose, and provides no means for easily placing a new, clean mask portion onto the handle portion. As with the previous example, the entire face mask would either need to be cleaned or replaced in the event that the mask portion became dirty, damaged, caked with hair treatments and/or discolored from hair dyes and similar products, or, alternatively, the mask would have to be disassembled and then reassembled in order to replace the mask portion.

U.S. Pat. No. 5,822,801 discloses another face shield having both a mask portion and a handle portion. The handle portion is integrally formed with the mask portion. U.S. Pat. No. 5,865,196 discloses a face shield having a mask portion and a handle portion rigidly attached to the mask portion. These devices both have the common shortcoming of not permitting a user to easily change mask portions when a particular mask portion becomes dirty, damaged or otherwise unusable; instead, such replacement would require disassembling and reassembling the device if such were possible at all.

With these considerations in mind, it is desirable to have a protective face shield with a mask portion and handle portion wherein the mask portion may easily be replaced on the handle portion, thus eliminating the need to clean or replace entire mask/handle combinations as with devices having mask portions and handle portions integrally formed or not easily disengaged and re-engaged from and to one another.

SUMMARY OF THE INVENTION

The subject invention is directed to a new and useful protective face shield, and particularly to a new and useful protective face shield for use in connection with the application of hair treatments.

In a preferred embodiment of the present invention, a protective face shield includes a mask portion and a handle portion. The mask portion has an exterior surface and an interior surface. The interior surface defines a cavity adapted to accept a substantial portion of a users face. The mask portion may include a ventilation structure to facilitate breathing and talking by the user. The ventilation structure may include a plurality of holes of any shape formed in the mask portion. The ventilation structure may be raised from the exterior surface of the mask portion, but does not need to be. The mask portion may also include a flange disposed about its periphery. Such a flange may render the mask more comfortable to a user during its use, and may also improve the protective qualities of the mask during use by, for example, improving the seal between a user's face and the mask.

The mask portion is readily operatively attachable to and removable from the handle portion, thereby allowing a user, such as a beauty salon technician, to easily remove a soiled or otherwise used mask portion form the handle portion and to replace on the handle portion a clean or otherwise unused mask portion. To facilitate attaching the mask portion to the handle portion, the mask portion may further include an anchoring structure, and the handle portion may be adapted for operatively accepting this anchoring structure. The anchoring structure may be in the form of a substantially planar tab extending substantially downward from the mask portion, or may be in any other form which permits the mask portion to be attached and removed readily from the handle portion, including multiple planar tabs, dowel-like structures, hooks, and velcro-type structures. In each case, the handle portion should include an appropriate structure or structures to receive or operate with the anchoring structure.

A preferred embodiment of the present invention may also include a bottom support surface disposed substantially at the bottom of the mask portion. This support surface may provide additional support to the mask portion when the mask portion is engaged with a handle portion by providing a surface on the mask portion which can rest on a corresponding support surface disposed substantially at the top of the handle portion.

In certain preferred embodiments of the subject invention, the handle portion includes a front portion and a rear portion, with the front portion and rear portion being adapted for securely maintaining the anchoring structure between them. Further preferred embodiments include a hinge or hinge structure in the handle portion which allows the front portion to move relative to the rear portion about the hinge or hinge structure. In this manner, the handle portion may transition from a closed orientation, in which it securely holds the mask portion, to an open orientation, in which it releases the mask portion.

The hinge structure may consist of an inner hinge element and at least two outer hinge elements. In such embodiments, the outer hinge elements may define a space there between, the space being dimensioned to operatively accept the inner hinge element. The inner hinge element may be a finger-like element. Alternatively, the hinge structure may be any structure which acts as a hinge or pivot, including but not limited to traditional pin hinges, pin-and-knuckle hinges, ball-and-socket joints, deformable plastic joints, and the like.

A preferred embodiment of the present invention includes a latch assembly adapted for maintaining the handle portion in a closed orientation and which may be operated to permit the handle portion to transition to an open orientation. The latch assembly may include a hook attached to one of either the front or rear handle portion. The hook may extend through an aperture in the other of the front or rear handle portion adapted for accepting the hook there through, and may abut a surface which is disposed adjacent to the aperture, thereby maintaining the handle in a closed orientation. Be pressing the hook downwardly from its normally upwardly-biased position, the hook may freely move through the aperture, thereby allowing the handle portion to transition from its closed orientation to its open orientation.

The latch assembly also may be any assembly which functions to securely maintain the handle portion in a closed orientation and which allows the handle to transition to an open orientation, including but not limited to magnetic assemblies, assemblies relying on friction and/or plastic deformation between elements, velcro-like structures, and the like.

These and other aspects of the subject invention will become more readily apparent to those having ordinary skill in the art from the following detailed description of the invention taken in conjunction with the drawings described herein.

BRIEF DESCRIPTION OF THE DRAWINGS

So that those having ordinary skill in the art to which the subject invention pertains will more readily understand how to make and use the subject invention, preferred embodiments thereof will be described in detail herein with reference to the drawings.

FIG. 8a is a front view of a portion of the hinge assembly of a preferred embodiment of the present invention.

FIG. 8b is a side view of a portion of the hinge assembly of a preferred embodiment of the present invention.

FIG. 9a is a front view of a portion of the latch assembly of a preferred embodiment of the present invention.

FIG. 9b is a side view of a portion of the latch assembly of a preferred embodiment of the present invention.

DETAILED DESCRIPTION OF THE PREFERRED EMBODIMENTS

Figure 1:
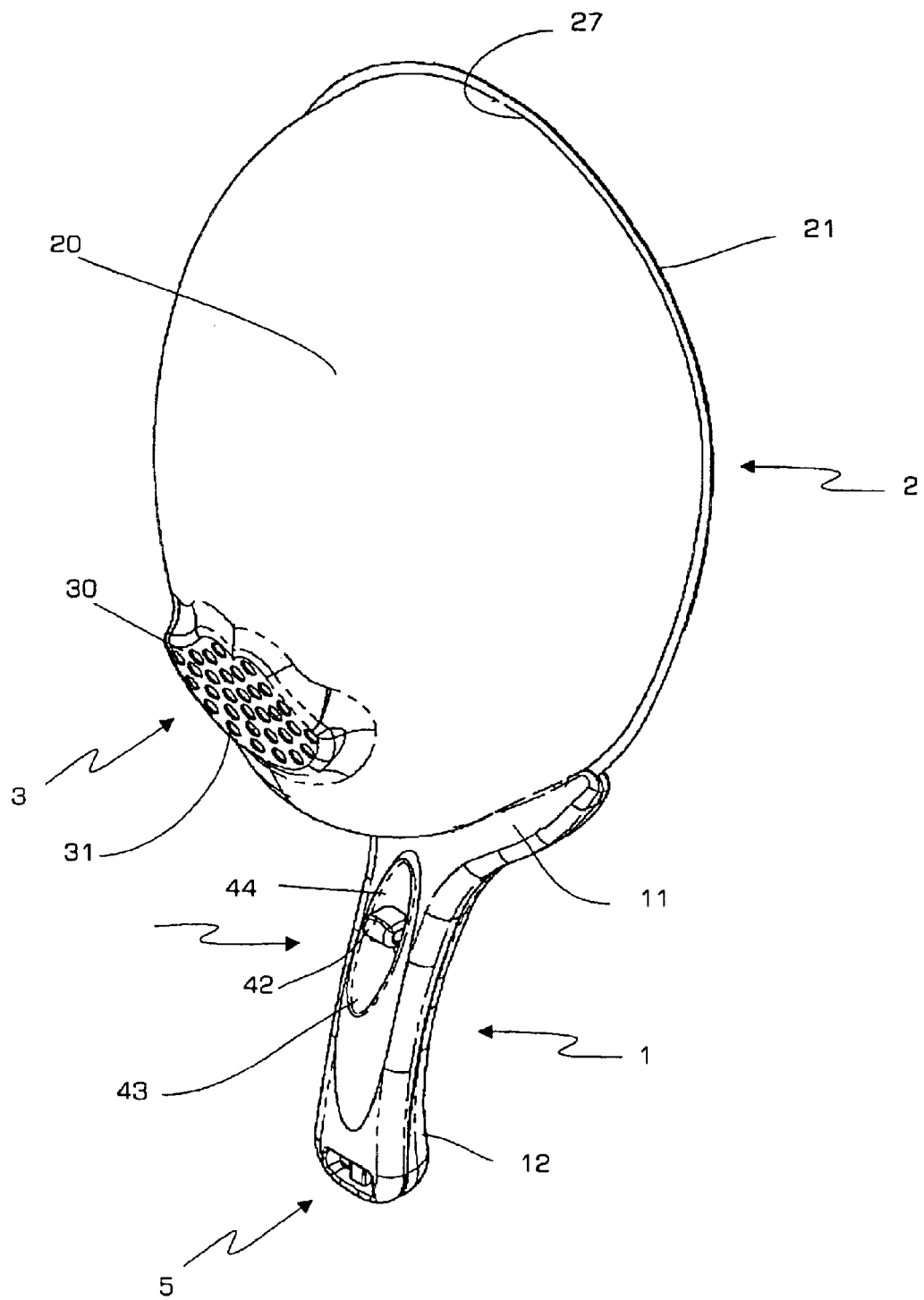
FIG. 1 is an isometric view of a preferred embodiment of the present invention.

Referring now in detail to the drawings wherein like reference numerals identify similar structural features of the several embodiments of the subject invention, there is illustrated in FIG. 1 an isometric view of a preferred embodiment of the present invention. Mask portion 2 is operatively connected to handle portion 1. Mask portion 2 includes ventilation structure 3 disposed generally in the lower portion of exterior surface 20, and includes ventilation holes 31 in the form of perforations contained in raised surface 30. Flange 21 extends around the periphery of mask portion 2.

Handle portion 1 includes front portion 11 and rear portion 12 operatively connected to one another by hinge assembly 5 and maintained in closed orientation by latch assembly 4. Latch assembly 4 includes concave portion 43 formed in front handle portion 11. Concave portion 43 contains aperture 42, through which hook 41 extends. Hook 41 is permanently affixed to rear handle portion 12, preferably integrally molded with rear handle portion 12, and is upwardly biased so as to maintain tight contact with surface 44, thereby maintaining handle portion 1 in a closed orientation. Hook 41 may be pressed downward so as to disengage from surface 44 and move through aperture 42, thereby permitting handle portion 1 to transition to an open orientation.

Figures 2, 3:
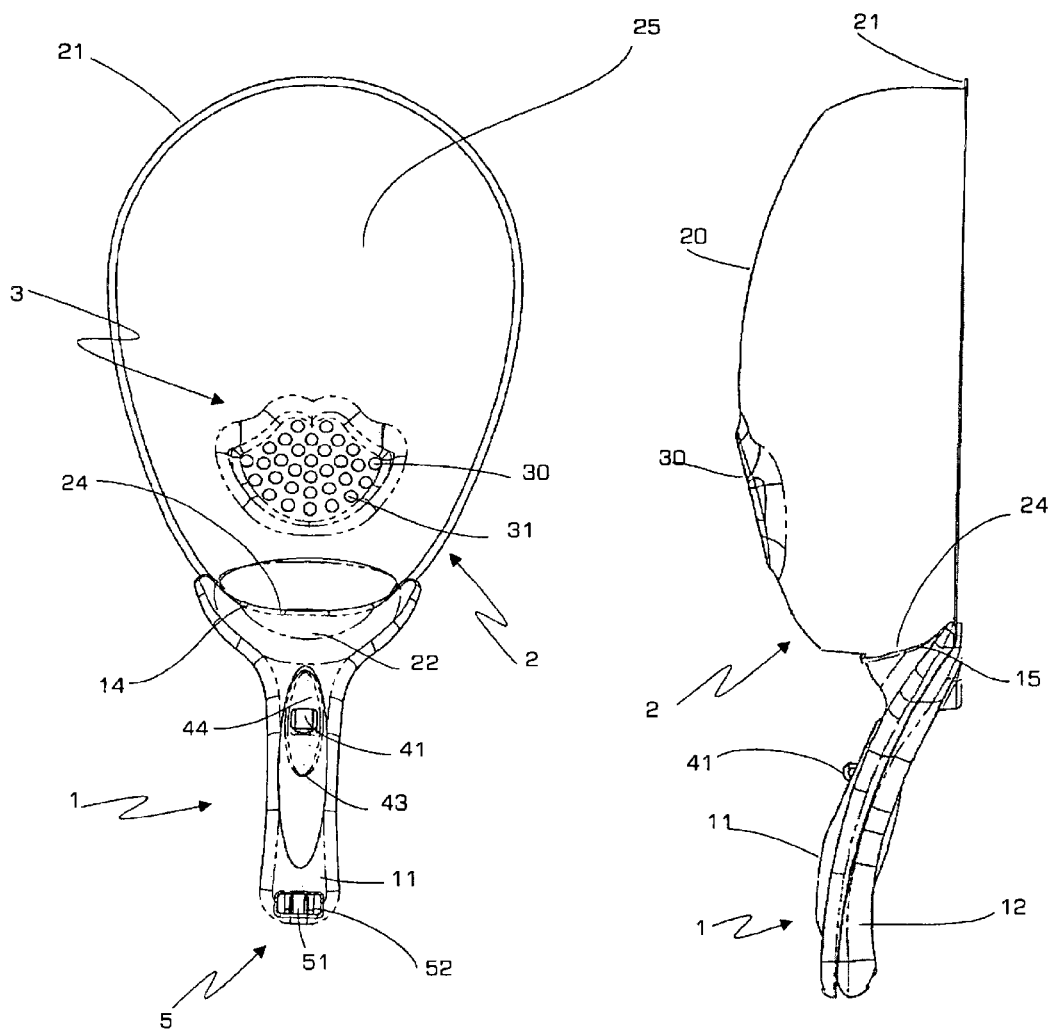
FIG. 2 is a frontal plan view of a preferred embodiment of the present invention.
FIG. 3 is a side plan view of a preferred embodiment of the present invention.

FIG. 2 shows a front plan view of a preferred embodiment of the present invention. Mask portion 2 is operatively connected to handle portion 1. Mask portion 2 includes ventilation structure 3 disposed generally in the lower front portion of exterior surface 20, and includes ventilation holes 31 in the form of perforations contained in raised surface 30. Flange 21 extends around the periphery of mask portion 2 at the trailing edge 27 of mask portion 2. Tab 22 extends downwardly from mask portion 2, where it is engaged between front handle portion 11 and the rear handle portion (not shown). When tab 22 is placed between front handle portion 11 and rear handle portion 12 and handle portion is placed into its closed orientation, front handle portion 11 and rear handle portion 12 actively clamp tab 22, effectively securing mask portion 2 to handle portion 1. Bottom support surface 24 of mask portion 2 is shaped so as to conform substantially with curved top portion 14 of handle portion 1.

Front handle portion 11 includes concave portion 43, which forms part of the latch assembly. Hook 41 extends through aperture 42 and abuts surface 44, maintaining the handle portion in a closed orientation.

Inner hinge element 51 is located in the bottom portion of handle portion 1 and extends from front handle portion 11. Inner hinge element 51 is operatively received between outer hinge elements 52, which define an interstitial space dimensioned so as to maintain inner hinge element 51 between outer hinge elements 52. Inner hinge element 51 and outer hinge elements 52 allow rotational movement of front handle portion 11 relative to rear handle portion 12 about the hinge assembly.

FIG. 3 shows a side plan view of a preferred embodiment of the present invention. Mask portion 2 is operatively coupled to handle portion 1, which is comprised of front portion 11 and rear portion 12. Hook 41 of the latch assembly extends through the aperture of the latch assembly (not shown). Bottom support surface 24 of mask portion 2 is supported on handle portion 1 on support surface 15 formed in the top of front handle portion 11.

Figure 4:
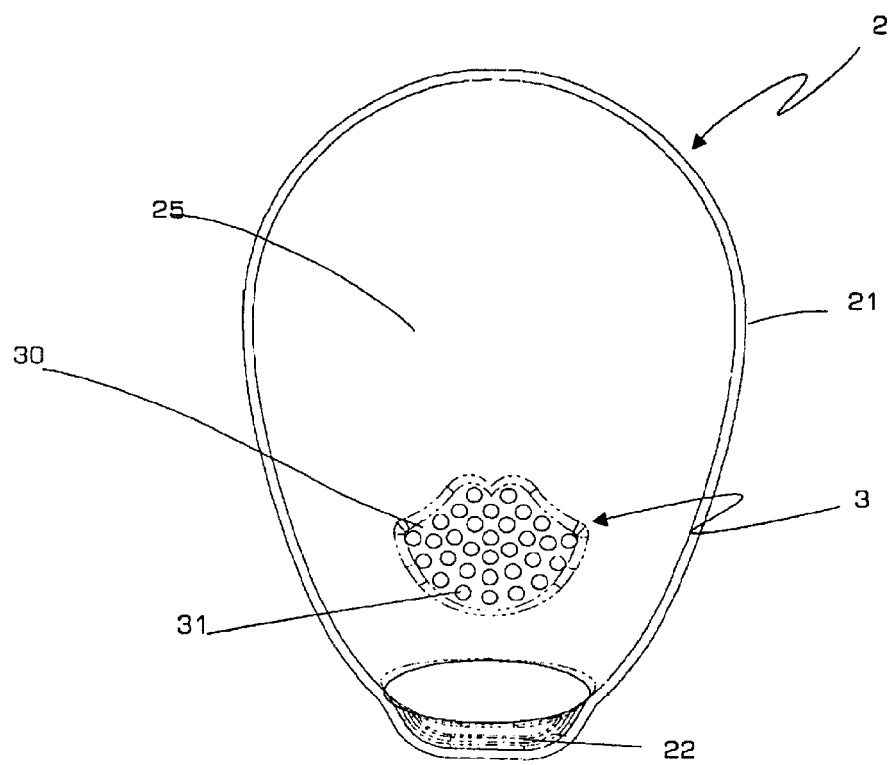
FIG. 4 is a rear plan view of the mask portion of a preferred embodiment of the present invention.

FIG. 4 shows a rear plan view of mask portion 2 of a preferred embodiment of the present invention. Ventilation structure 3 is disposed generally in the lower portion of interior surface 25, and includes ventilation holes 31 in the form of perforations contained in raised surface 30. Interior surface 25 is generally concave in shape, thus defining a cavity 26. Flange 21 extends around the periphery of mask portion 2. Tab 22 extends downwardly from mask portion 2.

Figure 5:
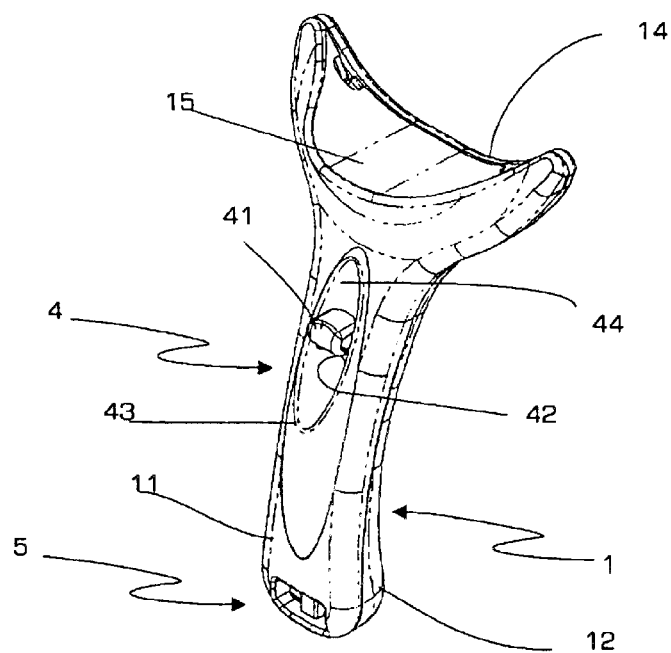
FIG. 5 is an isometric view of the handle portion of a preferred embodiment of the present invention.

FIG. 5 shows an isometric view of the handle portion of a preferred embodiment of the present invention. Front handle portion 11 includes concave portion 43, which in turn contains aperture 42, through which hook 41 extends, as described in greater detail above. Handle portion 1 includes curved top portion 14 formed in the top of both the front and rear handle portion. Support surface 15 is formed in the top of front handle portion 11. Together, curved top portion 14 and support surface 15 help to support a mask portion (not shown) that is operatively connected to handle portion 1.

Figure 6:
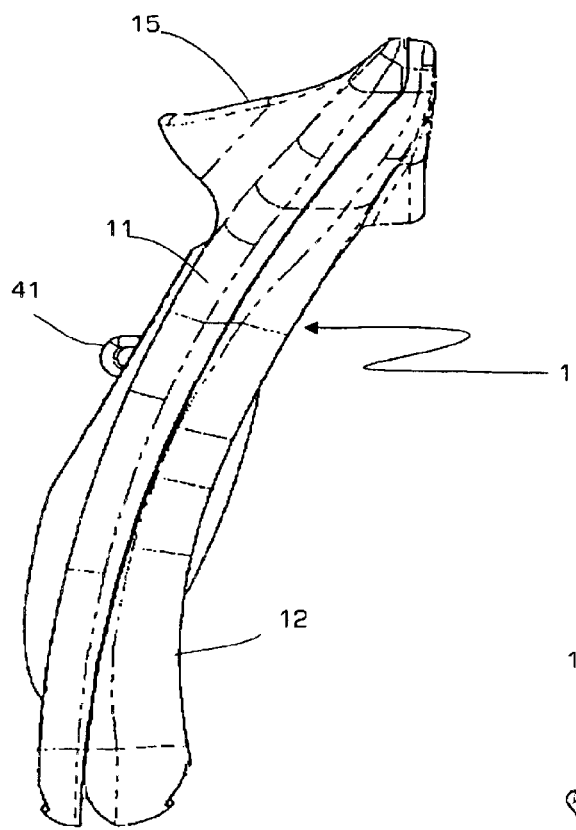
FIG. 6 is a side plan view of the handle portions of a preferred embodiment of the present invention shown in a closed orientation.
Figure 7:
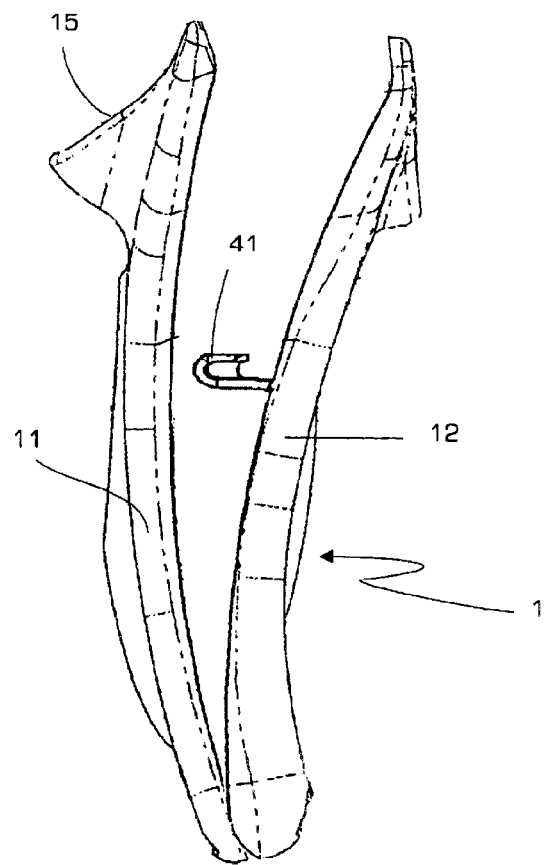
FIG. 7 is a side plan view of the handle portions of a preferred embodiment of the present invention shown in an open orientation.

FIGS. 6 and 7 are side plan views of the handle portions of a preferred embodiment of the present invention shown in closed and open orientations respectively. Front portion 11 is maintained abutted to rear portion 12 by hook 41 when in the closed position and is allowed to pivot about the hinge assembly (not shown) when hook 41 is pressed downward, thereby being allowed to move through the aperture (not shown) of the latch assembly and permitting the handle to transition to an open orientation. Support surface 15 is disposed at the top of front portion 11.

FIG. 8a shows a section of rear handle portion 12, at the bottom of which are disposed outer hinge elements 52. The space between outer hinge elements 52 is dimensioned to accept inner hinge element 51, shown in FIG. 8b in side view extending from front handle portion 11.

FIG. 9a shows a section of front handle portion 11. Concave portion 43 contains aperture 42 and surface 44. Hook 41, shown in FIG. 9b in side view extending from a section of rear handle portion 12, is permanently affixed to rear handle portion 12, and is preferably integrally molded with rear handle portion 12.

While particular embodiments of the present invention have been shown and described, it will be apparent to those skilled in the pertinent art that changes and modifications may be made without departing from the invention in its broader aspects.

What is claimed is:

1. A protective face shield comprising a mask portion and a handle portion, said mask portion having an exterior surface and an interior surface, said mask portion being readily operatively attachable to and removable from said handle portion, said interior surface defining a cavity adapted to accept a substantial portion of a users face, said mask portion including an anchoring structure, said handle portion being adapted for operatively accepting said anchoring structure to attach said mask portion to said handle portion, said handle portion including a front portion and a rear portion, said front portion and said rear portion being adapted for securely maintaining said anchoring structure there between.

2. The protective face shield of claim 1, wherein said handle portion includes a support surface disposed substantially at the top of said handle portion.

3. The protective face shield of claim 1, wherein said handle portion includes a hinge structure adapted for allowing said front portion to move relative to said rear portion about said hinge structure from a closed orientation to an open orientation.

4. The protective face shield of claim 3, wherein said hinge structure includes an inner hinge element and at least two outer hinge elements, said outer hinge elements defining a space there between, said space being dimensioned to operatively accept said inner hinge element.

5. The protective face shield of claim 1, wherein said handle portion includes a latch assembly, said latch assembly adapted for maintaining said handle portion in a closed orientation, said latch assembly being operable to allow said handle portion to transition from a closed orientation to an open orientation.

6. The protective face shield of claim 5, wherein said latch assembly includes a hook fixedly attached to one of said front portion and said rear portion of said handle portion, an aperture defined in the other of said front portion and said rear portion, said aperture adapted for accepting said hook there through, and a surface adjacent to said aperture, said hook being biased toward said surface so that said hook engages said surface to maintain said handle portion in a closed orientation.

7. The protective face shield of claim 1, wherein said handle portion includes a mask support surface disposed generally at the top said handle portion.

8. A protective face shield comprising:

a mask portion having:
an exterior surface and an interior surface, said interior surface defining a cavity adapted to accept a substantial portion of a users face,
a ventilation structure, said ventilation structure having a plurality of ventilation holes formed therein,
a substantially planar tab, said tab extending substantially downward from said mask portion, and
a bottom support surface disposed substantially at the bottom of said mask portion;

a handle portion having:
a front portion and a rear portion, said front portion and said rear portion being adapted for securely maintaining said planar tab of said mask portion there between;
a hinge disposed between said front portion and said rear portion, said hinge being adapted to allow said front portion to move relative to said rear portion about said hinge from a closed orientation to an open orientation;
a latch assembly, said latch assembly adapted for maintaining said handle portion in a closed orientation, said latch assembly being operable to allow said handle portion to transition from a closed orientation to an open orientation;

said mask portion being readily operatively attachable to and removable from said handle portion.

9. The protective face shield of claim 8, wherein said hinge includes an inner hinge element and at least two outer hinge elements, said outer hinge elements defining a space there between, said space being dimensioned to operatively accept said inner hinge element.

10. The protective face shield of claim 8, wherein said latch assembly includes a hook fixedly attached to one of said front portion and said rear portion of said handle portion, an aperture defined in the other of said front portion and said rear portion, said aperture adapted for accepting said hook there through, and a surface adjacent to said aperture, said hook being biased toward said surface so that said hook engages said surface to maintain said handle portion in a closed orientation.

* * * * *